(12) United States Patent
Guritza

(10) Patent No.: US 6,613,435 B1
(45) Date of Patent: Sep. 2, 2003

(54) BIO-SUPPORTIVE MATRICES, METHODS OF MAKING AND USING THE SAME

(76) Inventor: Dennis A. Guritza, 17727 Lost Trail, Chagrin Falls, OH (US) 44023

(*) Notice: Subject to any disclaimer, the term of this patent is extended or adjusted under 35 U.S.C. 154(b) by 11 days.

(21) Appl. No.: 09/697,811

(22) Filed: Oct. 26, 2000

Related U.S. Application Data

(60) Provisional application No. 60/161,501, filed on Oct. 26, 1999.

(51) Int. Cl.[7] ............................................... B32B 27/38
(52) U.S. Cl. .................. 428/413; 428/416; 523/122; 523/177; 523/428; 523/433; 523/458; 523/466; 427/386; 524/781
(58) Field of Search ................. 428/413, 416; 523/122, 177, 428, 433, 458, 466; 427/386; 524/781

(56) References Cited

U.S. PATENT DOCUMENTS

| | | | |
|---|---|---|---|
| 4,177,302 A | 12/1979 | Weiss | 427/407.1 |
| 4,197,233 A | 4/1980 | Marshall | 523/122 |
| 4,221,839 A * | 9/1980 | de Graaf | 428/213 |
| 4,260,700 A | 4/1981 | Cassutt et al. | 525/113 |
| 4,323,599 A | 4/1982 | Marshall | 427/181 |
| 4,428,989 A * | 1/1984 | Marshall | 428/35 |
| 4,521,475 A | 6/1985 | Riccio et al. | 428/142 |
| 4,561,981 A | 12/1985 | Characklis | 210/646 |
| 4,576,838 A | 3/1986 | Rosen et al. | 427/385.5 |
| 4,593,055 A | 6/1986 | Gitlitz et al. | 523/122 |
| 4,996,261 A | 2/1991 | Lebovitz et al. | 525/131 |
| 5,035,759 A | 7/1991 | Andoe | 156/64 |
| 5,116,407 A | 5/1992 | Hunter et al. | 106/16 |
| 5,246,489 A | 9/1993 | Farmer et al. | 106/18.33 |
| 5,284,587 A | 2/1994 | Wong et al. | 210/606 |
| 5,284,682 A * | 2/1994 | Martin | 427/386 |
| 5,336,304 A | 8/1994 | Andoe | 427/386 |
| 5,354,603 A * | 10/1994 | Errede | 428/240 |
| 5,403,390 A | 4/1995 | Spera et al. | 106/15.05 |
| 5,571,312 A | 11/1996 | Andoe | 106/18.32 |
| 5,693,527 A | 12/1997 | Imamura | 435/262 |
| 5,760,103 A * | 6/1998 | Wentzell | 523/122 |
| 5,814,172 A * | 9/1998 | Cox et al. | 156/71 |

* cited by examiner

Primary Examiner—Leszek Kiliman
(74) Attorney, Agent, or Firm—Hahn Loeser + Parks, LLP

(57) ABSTRACT

This invention relates to an article comprising a bio-supportive matrix comprising at least one bio-limiting agent and at least one nutritional source on a substrate. The invention also relates to the bio-supportive matrix and methods of using the matrix. The present invention can be used as a biological barrier to unwanted organisms, such as animals and plants, by producing allelochemicals that either kill or repel those organisms. The invention could be used as a coating on a vessel to prevent fouling of vessels. The invention may also be used to manufacture specific allelochemicals such as drugs or pharmaceuticals. The invention also relates to a method of preparing a bio-limiting ecological substrate useful as a means for producing allelochemicals, comprising the steps of providing a bio-supportive matrix as described above, and exposing the matrix to the environment, wherein the matrix is prepared to provide a biomass that produces the desired allelochemicals. The bio-supportive matrix provides a durable support layer for a biomass. The biomass may be selected to produce specific allelochemicals that have pharmaceutical or organism inhibiting properties.

60 Claims, 1 Drawing Sheet

BIO-SUPPORTIVE MATRICES, METHODS OF MAKING AND USING THE SAME

CROSS REFERENCE TO RELATED APPLICATION

This application claims priority from provisional application Ser. No. 60/161,501, filed Oct. 26, 1999, the entire disclosure of which is hereby incorporated by reference.

FIELD OF THE INVENTION

This invention relates to a bio-supportive medium and methods of making and using the same. More specifically, the invention relates to a polymeric matrix which contains at least one bio-limiting agent and at least one nutritional source.

BACKGROUND OF THE INVENTION

For 4000 years man has tried many varied means to manage the degradative effects of corrosion and consumption of man-made structures and vessels in both marine and freshwater aquatic environments. Early Egyptians clad their vessels with copper, centuries later mercury compounds were smeared on boats and nets to extend their useful life. Innovation has often come at critical times of newly recognized need. In times of war, military scientists sought means of improving speed and stealth. In energy limiting times, the 1970's, extreme toxins were used to eliminate any fouling which would increase drag on ships, raising operating cost by as much as 40%.

Over the last 30 years international focus on the environment has placed all previous methods of controlling corrosion and fouling in very bad light. Toxins with part per trillion toxicity have eradicated all life forms in harbors and estuaries in many ports of call in industrial countries of the world resulting in outright bans of their use. Assumed objectives for success, high levels of toxicity and narrowly defined specific means to achieve these results; control of release mechanisms simply through physical-chemical means has thwarted novelty. Concern for the environment has perceptively stymied all known approaches to provide safe and cost effective management of man made surfaces in both aquatic and hydrophytic environments. Dispersal of ecologically friendly toxins is an oxymoron.

For years, in the arena of allelochemistry, scientists have sought to provide an effective means of producing chemicals from biological sources in yields sufficient to be economically advantageous. Previously, chemical production involves culturing organisms in vats to produce a chemical through attempts at in-vitro (test tube like conditions) induced metabolism. The chemical is then harvested from the vats through typical chemical engineering means. Over specialization by both the chemist and the biologist has caused myopic views.

Allelochemicals are produced by biological organism(s) as a product of metabolism. These materials are generally referred to as either primary or more routinely secondary metabolites. They are often used by the organism outside the cell(s) of the organism(s) as bio-active agents. Historically they have been referred to as "chlorellin". The allelochemicals are often used by the organism as a chemical barrier or repellent to encroachment of other organism(s) in competition for resources including space (anchoring surface). The allelochemicals also inhibit consumption by invaders. Allelochemical production may be induced by internal or external stimuli. The allelochemicals may be defensive or offensive in nature. The allelochemicals are produced in response to environmental factors some of which include nutritional availability, light, temperature, etc. The organism(s), in anti-fouling applications are typically algae, diatoms, bacteria, often referred to as critters, produce these metabolites to ensure their effective competition for resources and physical space. Higher level invertebrates such as sponges, and other "soft bodied" sessile organisms are also found to provide abundant opportunities for allelochemical activity exploration, as well as any other life forms. Unfortunately, these allelochemicals typically have not been separated and used for specific commercial purpose due to the inability to provide suitable media and opportunity for further study and potential development. At the same time, absence of media for field research has prevented systematic searches for functional chemicals in a host of applications.

SUMMARY OF THE INVENTION

This invention relates to an article comprising a bio-supportive matrix comprising at least one bio-limiting agent and at least one nutritional source on at least one surface of a substrate. The invention provides for the creation of a matrix of commonly used components which interacts with the natural environment and becomes an interface which facilitates a selective biomass at equilibrium with the environment. The invention also relates to the bio-supportive matrix and methods of using the matrix. The present invention may be used as a biological barrier to unwanted organisms, such as animals and plants, by forming a biomass in a particular area, the biomass produces allelochemicals that either kill or more likely repel those unwanted organisms. The invention could be used as a coating on a vessel to prevent fouling, e.g., barnacle attachment of vessels. The invention may also be used to manufacture specific allelochemicals such as drugs or pharmaceuticals. The invention also relates to a method of preparing a bio-limiting matrix useful as a means for producing allelochemicals, comprising the steps of providing a bio-supportive matrix as described above, and exposing the matrix to the environment, wherein the matrix is prepared to support a biomass that produces the allelochemicals. The bio-supportive matrix provides a durable support layer for a biomass. The biomass may be selected to produce specific allelochemicals that have pharmaceutical or organism inhibiting and/or bio-active properties. The physical matrix and its components may be adjusted to select targeted species of organisms.

DETAILED DESCRIPTION OF THE PREFERRED EMBODIMENTS

Figure 1:
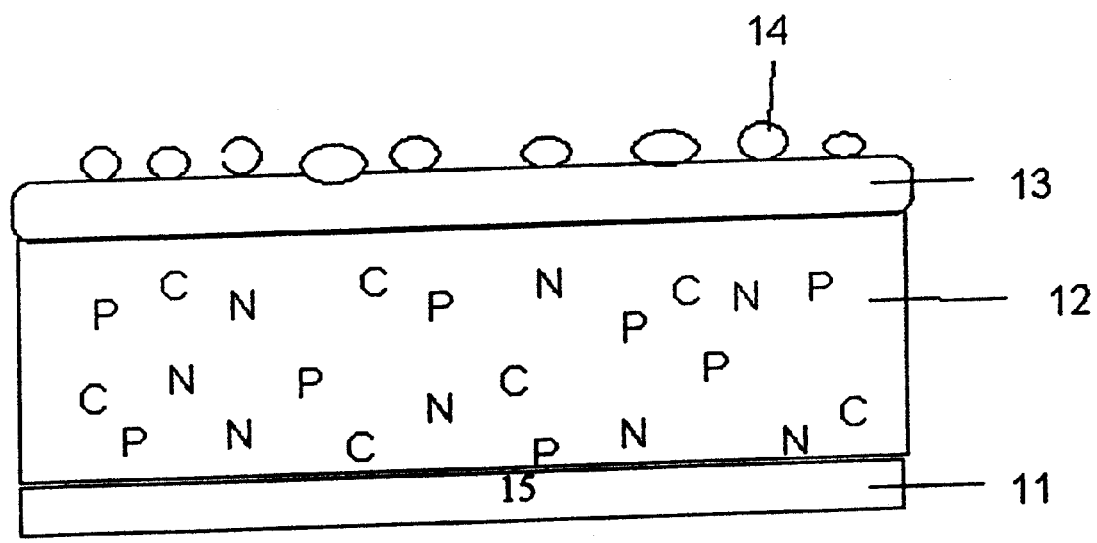
FIG. 1 is a cross section area of a bio-supportive matrix on a substrate.

In the specification and appended claims the term allelochemicals refers to the metabolic reaction products of a biomass. Typically the allelochemicals are secondary metabolite reaction product(s) of a biomass.

The term "bio-limiting chemical or agent" refers to a chemical which acts to have the effect of eliminating or altering the number and kinds of a specific group of biological organisms settling on or inhabiting the surface of the matric or a sub-habitat. The term "Bio-limiting effect" refers to the ability of an organism to produce and use such chemicals as allelochemicals to affect the response of another organism in competition for resources including space in the environment. The bio-limiting agent acts to alter the ability of undesired organisms to compete for resources in the local or surficial matrix environment. The term "biomass" refers to the biological organism(s) which are attached to or reside on the bio-supportive matrix. The biomass results from organisms that derive some portion of their nutrition from the bio-supporting matrix.

The bio-supportive matrix is biologically active. In other words, the matrix is effected by the biomass. In fact, the bio-supportive matrix is at least partially consumed by the bio-mass. The bio-supportive matrix is bio-degradable. The bio-supportive matrix is stenoprophiluric. Stenoprophiluric matrix is a matrix which is formed where the crystalline periodicity of the matrix is altered, either by designed polymerization or by interference of included or occluded agents in concert with a biologically active agent(s), facilitates the controlled degradation (biological, physical, & chemical) of the matrix at intergranular locations at such a rate that the biological agent limits. The matrix supports and enhances the development of a biomass different from a biomass that would result from the natural diversity of organisms occurring in the applied habitat. The bio-mass is consumed at a rate of about 0.1 to 10, or from about 0.5 to about 2, or from about 1 to about 1.5 mils per year.

As described above this invention relates to a bio-supportive matrix. The composition of bio-supportive matrix acts to limit the type of biological organisms (or biomass) which resides on and consumes the matrix. The matrix comprises a bio-limiting agent and a nutritional agent.

The bio-limiting agent may be present in any amount sufficient to limit the diversity of organism(s) and subsequently to prevent the inclusion of undesired biological organism(s) in the biomass. The bio-limiting agent may be present in an amount considered as little as ultra-trace to as much as that amount considered as a major component (nutrient), greater than 50% by weight relative to the bio-limiting action sought. In one embodiment, the bio-limiting agent is present in an amount of at least 2%, or at least about 5%, or at least about 10% by weight. The bio-limiting agent is present in an amount up to about 80%, or up to about 70%, or up to about 60% by weight. In some cases part per million concentrations of specific chemicals can account for limiting biological activity. One such concentration would include bio-limiting agents present from about 10 to about 1000, or from 50 to about 500 parts per million.

The bio-limiting agents include organic or inorganic bio-limiting agents. These material are present to provide an effect whereby desired organism's ability to compete for resources of the bio-matrix is improved. The bio-limiting agent may provide nutrition for one organism while concurrently being a toxin for another organism of similar or dissimilar species. The bio-limiting agent(s) are present in a form that is biologically available. The term bio-available refers to a bio-limiting agent, as well as a nutrient, which is available to interact or be metabolized by/with organisms to have its bio-limiting affect.

The bio-limiting agent may be organic or inorganic. Combinations of bio-limiting agents may be used. Examples of bio-limiting agents include heavy metals: lead, vanadium, molybdenum, nickel, tin, copper, mercury, etc. and alloys of two or more of those metals. The bio-limiting agents may be metal containing organic compounds such as organno-metallics of the aforementioned metals and their alloys. For instance, tin or copper compounds may be used as bio-limiting agents, often referred to as co-polymeric active ingredients. Additionally, metal free bio-limiting agents may be used. Examples of metal free bio-limiting agents include organic biocides such as isothiazolone, phenol compounds, such as coal tars, thiadiazole compounds, thiocarbamate compounds, etc. Bio-limiting agents may also be inorganic/organic compounds such as tri-butyl-tin. Any bio-limiting agent which assists in creating a modified or adapted bio-mass due to a new, or non-natural habitat or environment can be used.

A useful bio-limiting agent is copper. The copper is preferably in the form of copper metal particles. These particles have an average size of about 20 $\mu$m to about 41 $\mu$m. In one embodiment, the particles have a cuboidal shape. In one embodiment, copper or copper alloy pieces are produced by chopping wire, e.g. circular or square-section, such that the particles formed have a length substantially equal to their diameter or maximum cross- sectional dimension. Thus, solid lumps of copper are produced rather than flakes or elongate filaments or the like.

In one embodiment, the copper particles have a shape such that the ratios of their major dimensions are all in the range of about 0.7 to 1.0. Thus, for example, if the particles are laid on a flat horizontal surface, they are all of approximately the same dimensions in plane and elevation and, for each particle, its two major dimensions in plane (i.e. a first dimension being the length of the particle in plane and a second dimension being the width in plane measured at right angles to the first dimension) and its elevation will all be in a ratio of about 0.7 to 1.0 with respect to each other. The particles are thus solid lumps and not flakes or elongate filaments. Each of the particles may be of polyhedral shape, or more specifically in the form of a cube. Or, each of the particles may comprise a body having a rounded surface such as a cylinder or other shapes meeting this definition. Otherwise, the particles may comprise a mix of polyhedral bodies and bodies having rounded surfaces.

The bio-supportive matrix also contains at least one nutritional source. The nutritional source may be from the matrix polymer intrinsically, an additive in the matrix, or both. The nutrition source may be derived from any biologically available source in the matrix.

The bio-mass requires, for example carbon, phosphorus and/or nitrogen to sustain life. It may also require minor nutrients, trace (e.g., less than 0.5%) or even ultra-trace (e.g., less than 0.05%) nutrients for a desired application as well. The sources of carbon include the polymers of the matrix such as those described below. Carbon may also be provided by the components of the other nutrients, such as a phosphate compounds or a complexed amine compound. The sources of phosphorus include natural or synthetic polymer components, catalysts and additives, such as phosphate compounds and/or salts containing $PO_4$. Examples of sources of nitrogen include amines, catalysts, additives and occluded compounds, such as salts of nitrogen and ammonia. The amines may be mono or polyamines, including polyalkylene polyamines, such as diethylenetriamine, triethylenetetratamine, tetraethylenepentamine, etc. The nutritional additive(s) are present in amounts from ultra-trace levels to major source suppliers. Examples include selenium and zinc. When the nutrients are supplied as additives to the matrix, then they are present, in one embodiment, at a level of 1 to 500 parts per million.

The bio-supportive matrix includes a polymer or other supporting media, such as concrete. The polymers may be natural or synthetic polymers. The bio-supportive matrix could also include cementitious aggregates. The polymers can be bio-polymers or bio-engineered polymers. The polymer may be any polymer which can sustain the bio-supportive matrix. The polymer, by sustaining the bio-supportive matrix, provides the physical characteristics or environment needed to maintain the bio-limiting agent and other additives of the matrix as well as the biomass.

The bio-supportive matrix is consumed at a preferred rate by the biomass but still has sufficient hardness to provide durability to prevent destruction of the matrix. By altering the cross link density and/or the porosity and/or solubility, the bio-availability of the matrix material, nutrients and bio-limiting agents thereby form the bio-supportive matrix. Adjusting the stoichiometric ratios of the basic polymer system or by including or occluding additional components to the matrix desired properties can be achieved for various requirements. The durability of the bio-supportive matrix is related to its application. For instance, when used as a fouling coating, the bio-supportive matrix provides sufficient strength to prevent abrasion and therefore removal of the matrix from the surface to be protected from fouling organisms. In structural applications the matrix may be more resilient to provide 10 to 20 year service life with modified consumption rates where abrasion is less of a concern.

The polymers used may be any of those which are compatible with the bio-limiting agent and/or nutritional source. In one embodiment, the polymer is bio-degradable. It should be noted that in one embodiment, the polymer is a nutritional source for the biomass. These polymers include any natural or synthetic polymer including those used in fouling paints and coatings. The polymers may be polyepoxides, polyurethanes, polyesters, rubbers, Latex, styrene, elastomers, acrylics, acetoacetates, acetoacetamides, and bio-engineered polymers as well. In another embodiment, the matrix includes polymers or copolymers of acrylonitrile, methacrylonitrile, acrylamide, methacrylamide, vinyl chloride, vinyl acetate, acrylate, methacrylate, styrene, vinyl-isobutyl ether, benzaldimine, aldimine, araldimine, acetoacetoxyethymethacrylate, adimine, t-butylaminoethyl methacrylate, carboxyl groups, vinyltoluene-acrylate copolymers, epoxy- or coal tar epoxy-systems, etc. Other hydrophilic or partially hydrophilic polymers derived from modified blends such as other epoxies, urethanes (nitrogen source), rubbers, elastomers (carbon source), and bio-polymers (natural and synthetic, including bio-engineered) may also be used. Any blend or combination of components which facilitates the appropriate polymer degradation rate within a prescribed bio-agent dissolution or elution rate can work.

In one embodiment, the matrix contains a natural or synthetic rubber. Examples these rubbers include polysulfonated polyethylenes, of which Hypalon is one example, ethylene propylene diene monomers, styrene butadiene rubbers, bromobutyl rubber, chlorinated rubbers, such as chlorobutyl rubber, polychloroprenes such as Neoprene and nitrile rubbers.

In one embodiment, a catalyst or cross-linking agent such as polyethylene amines like tetra ethylene triamine (TETA) serve as a cross link modifier and a nutrient. The excess amine interferes with the polymerization increasing the porosity, lessening the cross-link density, and consequently the surface area where bio-degradation can occur at a favorable rate. The dissolution rate of occluded copper is approximately 10 to 20 micrograms of copper per day. Similar results may be obtained substituting a portion of the amine with other functional amine groups or catalysts employed as either physical property modifiers or cross link density adjustments.

In one embodiment, polymerization of a polymer contains functional acetoacetate groups with functional amines to form enamine complexes with bio-limiting agents. Single bio-active agents in part per million concentrations or as co-active agents in concert with any traditional anti-fouling agent(s) could likewise be used. In certain applications, blends with other traditional polymers and catalytic components and/or modifiers inert or active could provide additional beneficial properties.

In one embodiment, an epoxy matrix polymer with elution rates of copper between 30 and 50 micrograms per square centimeter per day is employed where genetically altered organisms are supported for studying new drug and fine chemical applications of allelochemicals occurring in such small and fragile concentrations that in-situ natural environmental habitats are required.

In one embodiment a urethane polymer with vanadium compounds as an active bio-limiting agent is utilized to eliminate the use of biocides in closed loop cooling water systems thereby averting the need to discharge biocides into the environment.

In one embodiment a coal tar polymer and copper metal is utilized on a concrete vault in a hydrophytic (wet submerged, tropical climate) environment protecting communication equipment and consumption of the concrete by native organisms.

In one embodiment, affixing a modified epoxy and copper metal matrix to a sheet or film is applied to the water line of a boat or vessel to impede settling of zebra mussels in fresh water habitats.

In one embodiment, an elastomer matrix with copper metal particles and a dispersal of isothiazolone in the matrix provides an excellent matrix for the protection and maintenance of wood members used in marina construction extending the useful life of the wood pilings and docks to 25 years. The isothiazolone enhances the biofouling control properties while the metal particles protect against marine boring organisms.

In another embodiment, the matrix contains an epoxy resin. The epoxy resin is prepared by reacting epoxy containing prepolymer and a crosslinking agent. Typically the epoxy resin is prepared from epichlorohydrin bis-phenol A and a suitable cross linking agent, such as an polyamine. The polyamines are described above. The amine is used in excess needed to react with the epoxy pre-polymer. The ratio of the amine to the epoxy pre-polymer is typically from about 0.75–4:1 or about 0.9–2, or about 1–1.5.

In one embodiment, the epoxy resins include any one of a number of well-known organic resins which are characterized by the presence therein of the epoxide group. A wide variety of such resins are available commercially. Such resins have either a mixed aliphatic-aromatic or an exclusively non-aromatic (i.e., aliphatic or cycloaliphatic) molecular structure.

The mixed aliphatic-aromatic epoxy resins are prepared by the well-known reaction of a bis(hydroxy-aromatic) alkane or a tetrakis-(hydroxyaromatic)-alkane with a halogen-substituted aliphatic epoxide, usually epichlorohydrin, in the presence of a base such as, e.g., sodium hydroxide or potassium hydroxide. Under these conditions, hydrogen halide is first eliminated and the aliphatic epoxide group is coupled to the aromatic nucleus via an ether linkage. Then the epoxide groups condense with the hydroxyl groups to form polymeric molecules which vary in size according to the relative proportions of reactants and the reaction time.

In lieu of the epichlorohydrin, one can use halogen-substituted aliphatic epoxides containing about 4 or more carbon atoms, generally about 4 to about 20 carbon atoms. In general, it is preferred to use a chlorine substituted terminal alkylene oxide (terminal denoting that the epoxide group is on the end of the alkyl chain) and a particular preference is expressed for epichlorohydrin by reason of its commercial availability and excellence in forming epoxy resins useful for the purpose of this invention.

If desired, the halogen substituted aliphatic epoxide may also contain substituents such as, e.g., hydroxy keto, nitro, nitroso, ether, sulfide, carboalkoxy, etc.

One can use bis-(hydroxyaromatic)alkanes containing about 16 or more carbon atoms, generally about 16 to about 30 carbon atoms such as, e.g., 2,2-bis(1-hy-droxy-4-naphthyl)propane; 2,2-bis(0-hydroxyphenyl) propane; 2,2-bis(p-hydroxyphenyl)butane, or 3,3-bis(p-hydroxyphenyl) hexane; and the like. If desired, the bis(hydroxyaromatic) alkane may contain substituents such as, e.g., halogen, nitro, nitroso, ether, sulfide, carboalkoxy, etc. In general, it is preferred to use a bis(p-hydroxyphenyl)alkane since compounds of this type are readily available from the well-known condensation of phenols with aliphatic ketones or aldehydes in the presence of a dehydrating agent such as sulfuric acid. Particularly preferred is 2,2-bis-(p-hydroxyphenyl)propane, which is available commercially as "Bisphenol A".

Epoxy resins which are especially suited for the purpose of the present invention are prepared by the reaction of bis-(hydroxyphenyl)alkane, preferably 2,2-bis-(p-hydroxyphenyl)propane with a chlorine substituted terminal alkylene oxide, preferably epichlorohydrin, to produce a product having an average molecular weight within the range of about 300 to about 500 and preferably about 350 to about 400. One of such preferred epoxy resins having an average molecular weight of about 380 and prepared from 2,2-bis-(p-hydroxyphenyl)-propane and epichlorohydrin is known by the trade designation "Epon 1031." Another general class of epoxy resins which are useful for the purpose of the present invention are the aliphatic or cycloaliphatic epoxy resins. These resins, which are cyclic or acyclic olefins such as, e.g., methylcyclohexane, vinylcyclohexene, alphamethyl-vinyl-cyclohexene, polybutadiene, etc., which contain at least one carbon-to-carbon multiple bond. One of such non-aromatic epoxy resins, known by the trade designation "Oxiron 2001", is made by oxidizing polybutadiene with peracetic acid. Still another class of epoxy resins which are useful for the purposes of the present invention are the novolak resins. Representative of the novolak resins are the phenol novolak and cresol novolak resins.

The epoxy resins can be modified by the addition of various monomers and polymers which effect desirable properties in the cured epoxy system. For example, the thermal stability of the epoxy system can be increased by mixing various monomers with the epoxy resin-oxidizing agent mixture. These mixtures then can be cured with sulfur dioxide in the manner described above.

Examples of monomeric materials which can be blended with the acid-curable epoxy resins in accordance with this invention include acrylic or vinyl monomers, furfuryl alcohol, polyfurfuryl alcohol, a formaldehyde based thermosetting resin, urethane resin, or mixtures thereof. The exact mechanism by which these specified monomers and polymers modify the properties of the acid curable epoxy resins is not known at this time. It has been found that up to about 50% by weight of the above-specified monomers and polymers can be mixed with the epoxy resin to form modified epoxy resin systems in accordance with the invention. Acrylic compounds are particularly useful as modifiers for the epoxy systems, and specific examples include trimethylol propane triacrylate and furfuryl methacrylate. Examples of the formaldehyde-based thermosetting resins useful as modifiers include phenol-formaldehyde resin or urea formaldehyde resin. Resorcinol also is a particularly useful modifying agent.

Examples of the polyhydric alcohols are those containing from 2 to about 10 hydroxy groups. These are illustrated, for example, by the alkylene glycols and polyoxyalkylene glycols such as ethylene glycol, diethylene glycol, triethylene glycol, tetraethylene glycol, dipropylene glycol, tripropylene glycol, dibutylene glycol, tributylene glycol, and other alkylene glycols and polyoxyalkylene glycols in which the alkylene radicals contain 2 to about 8 carbon atoms.

As described herein the bio-supportive matrix contains nutritional additives and bio-limiting agents. The matrix typically has a thickness from 2 or 3 mils (thousandths of an inch) to a matrix 40 or 50 mils. The matrix is consumed by the biomass over extended periods of time while at equilibrium with the external environment and the bio-limited biomass as allelochemicals are produced.

The bio-supportive matrix is supported by or on a substrate. The substrate may be a vessel hull, like that of a boat or ship. The boat hulls may be made of wood, fiberglass, aluminum or steel, or hulls having a rubberized coating. The bio-supportive matrix may also be applied to other marine structures, such as pilings, floats, and buoys made of the above listed materials or concrete. The substrate may also be any surface which supports the bio-supportive matrix and which provides the needed structural support for the matrix and biomass. The substrate could be a culvert or piping that provides a support for the bio-supportive matrix and biomass. A resultant biological barrier (biomass, bio-film) may be established using the bio-supportive matrix, biomass and substrate. The substrate may also be a structural support or surface expanding area as in a vessel such as a fermentation vessel. The substrate could be any existing structure in an aqueous or hydrophytic environment. The substrate could be a sheet, film, or cast form. Allelochemicals may be separated from the biomass as they are produced.

In reference to FIG. 1, a bio support matrix is shown having substrate 11 which is adhered to bio-supportive matrix 12. Matrix 12 contains carbon (C), nitrogen (N) and phosphorus (P). The matrix 12 supports biomass 13 which in turn produces allelochemicals 14.

The bio-support matrix is made by selecting a base matrix material which can support biomass sustenance for naturally occurring organism(s) in the presence bio-limiting agent(s) causing a biomass which sustains selective development. Bis-phenol A resins polymerized with the blending of glycols, amines and copper metal particles, provides a carbon and nitrogen nutrient source to naturally occurring organisms while limiting the numbers and kinds of organisms which aggregate on the matrix due to the bio-limiting conditions created by the presence of biologically available and bio-limiting amounts of copper. The criteria for success is a matrix which can be degraded by naturally occurring organisms at a reasonable rate to provide long term support for continued growth of the remaining bio-limited species while under the bio-limiting conditions of the agent. In this case a cross link interference is created with excess amines and heavy inclusions of specific copper metal particles of pre-determined shape and concentration such as to permit surface area and nutrients while limiting the numbers and kinds of subsequent organisms in the biomass by the amount (bio-available concentration) of copper at the matrix interface. A workable formulation can be prepared by using two premix epoxy components. Part A to be resin such as one part (1) Araldite 508 to 0.43 parts Araldite 6004 (polyglycidal blend for flexibility and hydrophilicity) pre-reacted to form adducts with 1.5 stoichiometric amine such as triethylenetetraamine. Copper particles as M-357 with smooth cuboidal particle shapes to permit appropriate flow rheology for spray applications is added to the non-amine adduct to comprise 55% of the resultant mixture by weight. Solvent diluents may be used such as 1:1:1 MEK:TOL:XYL typically from 5 to 12% dependent on application conditions. In this case, adjusting the admix ratio to 4:1 with pre-reaction permits the-final matrix cross-link to be such that sufficient surface area, bio-available & bio-limiting agent (copper) is dispersed throughout the matrix, and nutrients are available to a biomass.

The above bio-supportive matrix is employed by adding the matrix to a boat hull with appropriate base adhesion coat and mid-coat for corrosion and insulation barriers to bimetallic galvanic actions, to prevent adherence of barnacles and other undesirable organisms. Another application is to apply the matrix, over a filler base coat, to a culvert to prevent organism from migrating from one field to another.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. An article comprising a bio-supportive matrix comprising at least one bio-limiting agent and at least one nutritional source on a substrate, wherein the bio-supportive matrix is adapted to supporting a biomass.

2. The article of claim 1 wherein the bio-limiting agent is a metal or organic toxin.

3. The article of claim 1 wherein the bio-limiting agent includes a tin, copper, or nickel metal, alloy or organic complex.

4. The article of claim 1 wherein the bio-limiting agent is a copper or copper alloy particle.

5. The article of claim 1 wherein the nutritional source includes a source of carbon, nitrogen and phosphorus.

6. The article of claim 1 wherein the nutritional source is a nitrogen and carbon containing polymer.

7. The article of claim 6 wherein the carbon and nitrogen containing polymer is a polyepoxide or polyurethane.

8. The article of claim 7 wherein the polymer is a crosslinked polyepoxide prepared from an epoxy resin and a polyamine crosslinking agent.

9. The article of claim 1 wherein the bio-supportive matrix contains at least one crosslinked-modified polymer.

10. The article of claim 9 wherein the polymer is selected from polyepoxides, polyester, polyurethanes, or rubbers.

11. The article of claim 6 wherein the polymer of the matrix is a polymer or copolymer of acrylonitrile, methacrylonitrile, acrylamide, methacrylamide, vinyl chloride, vinyl acetate, acrylates or methacrylate or styrenes.

12. The article of claim 1 further comprising a biomass on the biosupportive matrix.

13. The article of claim 12 wherein the biomass consumes the biosupportive matrix.

14. The article of claim 1 wherein the substrate is a metal or fiberglass vessel.

15. A bio-supportive matrix including a bio-limiting agent, and a nutritional source, wherein the bio-supportive matrix is adapted to supporting a biomass.

16. A method of preventing fouling comprising the steps of providing a bio-supportive matrix comprising a bio-limiting agent and at least one nutrition source, wherein the biosupportive matrix is adapted to supporting a biomass, and applying the coating to a substrate, wherein a biomass forms on the bio-supportive matrix.

17. The method of claim 16 wherein the biomass produces at least one allelochemical that inhibits attachment of fouling organisms.

18. The method of claim 16 wherein the substrate is metal, fiberglass, wood, cement or a combination thereof.

19. The method of claim 16 wherein the substrate is a boat hull.

20. The method of claim 16 wherein the substrate is a cement support.

21. A method of preventing migration of organisms comprising the steps of (A) providing a bio-supportive matrix comprising a nutritional source and a bio-limiting agent, wherein the bio-supportive matrix is biodegradable, and (B) applying the bio-supportive matrix to a substrate wherein a biomass forms on the biosupportive matrix and the biofilm produces allelochemicals to provide a barrier to organism migration.

22. A method of producing allelochemicals comprising the steps of providing a bio-supportive matrix comprising a nutritional source and a bio-limiting agent on the substrate, exposing the bio-supportive matrix to an environment which causes formation of a biomass that produces allelochemicals, and removing the allelochemicals produced by the biomass.

23. The article of claim 1 wherein the biomass consumes the bio-supportive matrix.

24. The article of claim 1 wherein the biosupportive matrix has a thickness from 2 to 50 mils.

25. The article of claim 6 wherein the carbon and nitrogen containing polymer is selected from polyepoxides, polyurethanes, polyesters, rubbers, Latex, styrene, elastomers, acrylics, acetoacetates, acetoacetamides, and bio-engineered polymers.

26. The article of claim 6 wherein the carbon and nitrogen containing polymer is selected from polymers or copolymers of acrylonitrile, methacrylonitrile, acrylamide, methacrylamide, vinyl chloride, vinyl acetate, acrylate, methacrylate, styrene, vinyl-isobutyl, either, benzaldimine, aldimine, araldimine, acetoacetoxyethymethacrylate, adimine, t-butylaminoethyl methacrylate, carboxyl groups, vinyltoluene-acrylate copolymers, and epoxy-or coal tar epoxy-systems.

27. The article of claim 6 wherein the carbon and nitrogen containing polymer is a polyepoxide.

28. The article of claim 1 wherein the substrate is metal, fiberglass, wood, cement or a combination thereof.

29. The article of claim 1 wherein the substrate is a boat hull.

30. The article of claim 1 wherein the substrate is a cement support.

31. An article comprising a bio-supportive matrix comprising at least one bio-limiting agent and at least one polyexpoxide on a substrate, wherein the bio-supportive matrix is adapted to supporting a biomass.

32. The article of claim 31 wherein the bio-limiting agent is a metal or organic toxin.

33. The article of claim 31 wherein the bio-limiting agent includes a tin, copper, or nickel metal, alloy or organic complex.

34. The article of claim 31 wherein the bio-limiting agent is a copper or copper alloy particle.

35. The article of claim 31 wherein the polyepoxide is a crosslinked polyepoxide prepared from an epoxy resin and a polyamine crosslinking agent.

36. The article of claim 31 wherein the biosupportive matrix has a thickness from 2 to 50 mils.

37. The article of claim 31 further comprising a biomass on the bio-supportive matrix.

38. The article of claim 37 wherein the biomass consumes the bio-supportive matrix.

39. The article of claim 31 wherein the substrate is a metal or fiberglass vessel.

40. The article of claim 31 wherein the substrate is a boat hull.

41. The article of claim 31 wherein the substrate is a cement support.

42. The matrix of claim 15 wherein the bio-limiting agent is a metal or organic toxin.

43. The matrix of claim 15 wherein the bio-limiting agent includes a tin, copper, or nickel metal, alloy or organic complex.

44. The matrix of claim 15 wherein the bio-limiting agent is a copper or copper alloy particle.

45. The matrix of claim 15 wherein the nutritional source includes a source of carbon, nitrogen and phosphorus.

46. The matrix of claim 15 wherein the nutritional source is a nitrogen and carbon containing polymer.

47. The matrix of claim 15 wherein the biomass consumes the bio-supportive matrix.

48. The matrix of claim 15 wherein the biosupportive matrix has a thickness from 2 to 50 mils.

49. The matrix of claim 46 wherein the carbon and nitrogen containing polymer is selected from polyepoxides, polyurethanes, polyesters, rubbers, Latex, styrene, elastomers, acrylics, acetoacetates, acetoacetamides, and bio-engineered polymers.

50. The matrix of claim 46 wherein the carbon and nitrogen containing polymer is selected from polymers or copolymers of acrylonitrile, methacrylonitrile, acrylamide, methacrylamide, vinyl chloride, vinyl acetate, acrylate, methacrylate, styrene, vinyl-isobutyl ether, benzaldimine, aldimine, araldimine, acetoacetoxyethymethacrylate, adimine, t-butylaminoethyl methacrylate, carboxyl groups, vinyltoluene-acrylate copolymers, and epoxy-or coal tar epoxy-systems.

51. The matrix of claim 46 wherein the carbon and nitrogen containing polymer is a polyepoxide.

52. The matrix of claim 15 wherein the bio-supportive matrix contains at least one crosslinked-modified polymer.

53. The matrix of claim 52 wherein the polymer is selected from polyepoxides, polyester, polyurethanes, or rubbers.

54. The matrix of claim 43 wherein the polymer is a crosslinked polyepoxide prepared from an epoxy resin and a polyamine crosslinking agent.

55. A bio-supportive matrix comprising a bio-limiting agent, and a polyepoxide, wherein the bio-supportive matrix is adapted to supporting a biomass.

56. The matrix of claim 55 wherein the bio-limiting agent is a metal or organic toxin.

57. The matrix of claim 55 wherein the bio-limiting agent includes a tin, copper, or nickel metal, alloy or organic complex.

58. The matrix of claim 55 wherein the bio-limiting agent is a copper or copper alloy particle.

59. The matrix of claim 55 wherein the biosupportive matrix has a thickness from 2 to 50 mils.

60. The matrix of claim 55 wherein the polyepoxide is prepared from an epoxy resin and a polyamine crosslinking agent.

\* \* \* \* \*